United States Patent
Hong et al.

(10) Patent No.: US 7,863,569 B2
(45) Date of Patent: Jan. 4, 2011

(54) APPARATUS FOR ANALYZING CELLS IN REAL-TIME

(75) Inventors: Sung Min Hong, Gyeonggi-do (KR);
Soon Sup Park, Gyeonggi-do (KR);
Yeon Hwa Kwak, Gyeonggi-do (KR);
Yeon Shik Choi, Gyeonggi-do (KR);
Han Young Lee, Gyeonggi-do (KR);
Hyung Man Lee, Gyeonggi-do (KR)

(73) Assignee: Korea Electronics Technology Institute (KR)

( * ) Notice: Subject to any disclaimer, the term of this patent is extended or adjusted under 35 U.S.C. 154(b) by 119 days.

(21) Appl. No.: 12/168,392

(22) Filed: Jul. 7, 2008

(65) Prior Publication Data
US 2009/0008559 A1 Jan. 8, 2009

(30) Foreign Application Priority Data
Jul. 6, 2007 (KR) .................. 10-2007-0068360

(51) Int. Cl.
*G01J 5/02* (2006.01)
(52) U.S. Cl. ................................. 250/339.06
(58) Field of Classification Search ............ 250/339.06
See application file for complete search history.

(56) References Cited

U.S. PATENT DOCUMENTS

| | | | | |
|---|---|---|---|---|
| 5,754,335 A * | 5/1998 | Takagi et al. | ................ | 359/368 |
| 5,923,036 A * | 7/1999 | Tague et al. | ............ | 250/339.07 |
| 6,094,300 A * | 7/2000 | Kashima et al. | ............. | 359/385 |
| 6,215,588 B1 * | 4/2001 | Wachi | ........................ | 359/368 |
| 6,275,294 B1 * | 8/2001 | Folestad | ..................... | 356/432 |
| 6,836,497 B1 * | 12/2004 | Hatori | ..................... | 372/43.01 |
| 2002/0141040 A1 * | 10/2002 | Fujiura et al. | ............... | 359/326 |

\* cited by examiner

*Primary Examiner*—David P Porta
*Assistant Examiner*—Marcus H Taningco
(74) *Attorney, Agent, or Firm*—Thomas, Kayden, Horstemeyer & Risley, LLP.

(57) ABSTRACT

The present invention relates to an apparatus for analyzing cells in real-time which incorporates a wavelength-tunable light source/infrared ray (IR) sensor and can be used to observe and analyze the IR-related characteristics of adherent cells or non-adherent cells. The Apparatus for analyzing cells in real-time in accordance with the present invention can be used to quantify specific materials in a cell and measure the metabolism of a cell. In addition, the apparatus for analyzing cells in real-time in accordance with the present invention can be configured to have a visible light microscope coupled thereto, and in this configuration, it can be used to locate a cell of interest.

7 Claims, 3 Drawing Sheets

APPARATUS FOR ANALYZING CELLS IN REAL-TIME

BACKGROUND OF THE INVENTION

1. Field of the Invention

The present invention relates to an apparatus for analyzing cells in real-time; and more particularly, to an apparatus for analyzing cells in real-time which incorporates a wavelength-tunable light source/infrared ray (IR) sensor and can be used to observe and analyze the infrared ray (IR)-related characteristics of adherent cells or non-adherent cells.

2. Background of the Related Art

Any discussion of the prior art throughout the specification should in no way be considered as an admission that such prior art is widely known or forms part of common general knowledge in this field.

In using conventional laser capture microdissection (LCM) systems for IR measurement, a tissue of interest is mounted on a slide glass under a usual microscope, and a transfer film, which is a thermoplastic film, is placed on it and then a part of the transfer film which is activated by laser beam expands to get fused to cells of interest of the underlying tissue. In this way, the conventional LCM systems for IR measurement can be used to obtain only cells of interest. The apparatuses for such systems enable an operator to select only cells of interest and extract several cells easily using a continuous laser emission mode. And the conventional apparatuses are operated with low power IR to protect a specimen.

However, the conventional apparatuses can not be used to analyze IR characteristics which a cell shows in response to changes of external environments. Especially, they can not be used in chemotaxis experiments for analyzing reactions of cells to chemicals. In addition, the conventional apparatuses have disadvantages in that specific materials inside cells can not be easily quantified and long-time observation can not be made using them. These disadvantages, namely difficulties in quantification of specific materials in cells and long-time observation, are more conspicuous in case of using a usual fluorescent microscope.

SUMMARY OF THE INVENTION

Accordingly, the present invention is directed to an apparatus for analyzing cells in real-time which incorporates a wavelength-tunable light source/infrared ray (IR) sensor and the present invention substantially obviates one or more problems due to limitations and disadvantages of the related art.

It is an object of the present invention to provide an apparatus for analyzing cells in real-time which incorporates a wavelength-tunable light source and an IR sensor and can quantify specific materials in a cell to provide digital values so that metabolism of the cell can be analyzed.

Another object of the present invention is to provide an apparatus for analyzing cells in real-time which a visible light microscope is coupled with. Using the apparatus coupled with a visible light microscope for selecting specific cells, cells with specific growth or physical characteristics in various culture conditions can be selectively analyzed for a long time. Especially adherent cells or non-adherent cells with a specific velocity—a distance a cell migrates for a cell culture time—can be distinguished and analyzed using the apparatus coupled with a visible light microscope.

To accomplish the above objects, according to the present invention, there is provided an apparatus for analyzing cells in real-time which comprises a platform for a sample to be placed on; an IR observation unit for observing the sample using IR, the IR observation unit comprising a wavelength-tunable light source unit for irradiating light to a specific area of the sample, an IR sensing unit for receiving the light irradiated from the wavelength-tunable light source unit, and an image sensing unit for alignment for identifying the area of the sample which is being irradiated by the light from the wavelength-tunable light source unit; and a signal processing unit for processing an IR signal received from the IR observation unit.

At this time, it is preferable that the IR sensing unit further comprises a filter for filtering the light which has passed through the sample to get a predetermined wavelength band thereof to pass through; and a detector for receiving the light which has passes though the filter and generating an IR signal. In addition, the IR sensing unit can further comprise a light condensing means for condensing the light which has passed through the filter or the sample to the IR detector.

In the apparatus for analyzing cells in real-time in accordance with the present invention, the platform preferably comprises a sample position controlling stage for controlling position of the sample.

In the apparatus for analyzing cells in real-time in accordance with the present invention, the wavelength-tunable light source unit is preferably installed in a way to control positions or directions of light irradiation.

In the apparatus for analyzing cells in real-time in accordance with the present invention, it is preferable that the IR sensing unit further comprises a sensor position controlling means for controlling positions of the filter, the light condensing means and the detector.

It is preferable that the apparatus for analyzing cells in real-time in accordance with the present invention further comprises a microscope unit for an operator to observe the cells of the sample therethrough. At this time, the microscope unit and the IR observation unit are connected to each other in such a way that they can move between a location for microscope observation and a location for IR measurement, separated in a predetermined distance from each other. Here, in the location for microscope observation, the apparatus for analyzing cells in real-time is used for observation of the sample by the microscope unit and, in the location for IR measurement, the apparatus for analyzing cells in real-time is used for measurement of the sample by the IR observation unit.

In the apparatus for analyzing cells in real-time in accordance with the present invention, it is preferable that the area of the sample which is observed by the microscope unit in the location for microscope observation has the same center as that of the area which is photographed by the image sensing unit for alignment in the location for IR measurement.

It is preferable that the apparatus for analyzing cells in real-time in accordance with the present invention further comprises an image sensor which is coupled to an ocular lens of the microscope unit; and an image processing unit for processing an image signal received from the image sensor.

In accordance with the present invention, the image processing unit preferably comprises a black/white conversion means for binary processing of the image signals of the cells in the sample; an individual recognizing means for recognizing individual cells using a lightness difference in the boundaries of the images which has been black/white conversed by the black/white conversion means; and a recognition factor providing means for providing a recognition factor to each of the individual cells.

It is preferable that the apparatus for analyzing cells in real-time in accordance with the present invention further comprises an position change measuring means for measuring a change in a cell's position using a variation in values of centers of gravity of the cell, from the images processed in the image processing unit.

It is preferable that the apparatus for analyzing cells in real-time in accordance with the present invention further comprises a controlling unit. In the location for microscope observation, the controlling unit receives information on a recognition factor which the recognition factor providing means provides for a specific individual cell; receives information on a positional change of the cell from the position change measuring means; changes positions of the platform or the microscope unit at set time intervals or in case that the cell moves beyond a set range so that the individual cell can be located within the area which is being observed using the microscope; and controls to move the IR observation unit to the location for IR measurement at set time intervals and then controls the wavelength-tunable light source unit to irradiate light to the individual cell; and controls to the signal processing unit to process an IR signal.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE PREFERRED EMBODIMENT

The present invention will now be described more fully with reference to the accompanying drawings, in which exemplary embodiments of the invention are shown. The invention may, however, be embodied in many different forms and should not be construed as being limited to the embodiments set force herein, rather, these embodiments are provided so that this disclosure will be thorough and complete, and will fully convey the concept of the invention to those skilled in the art.

Figure 1:
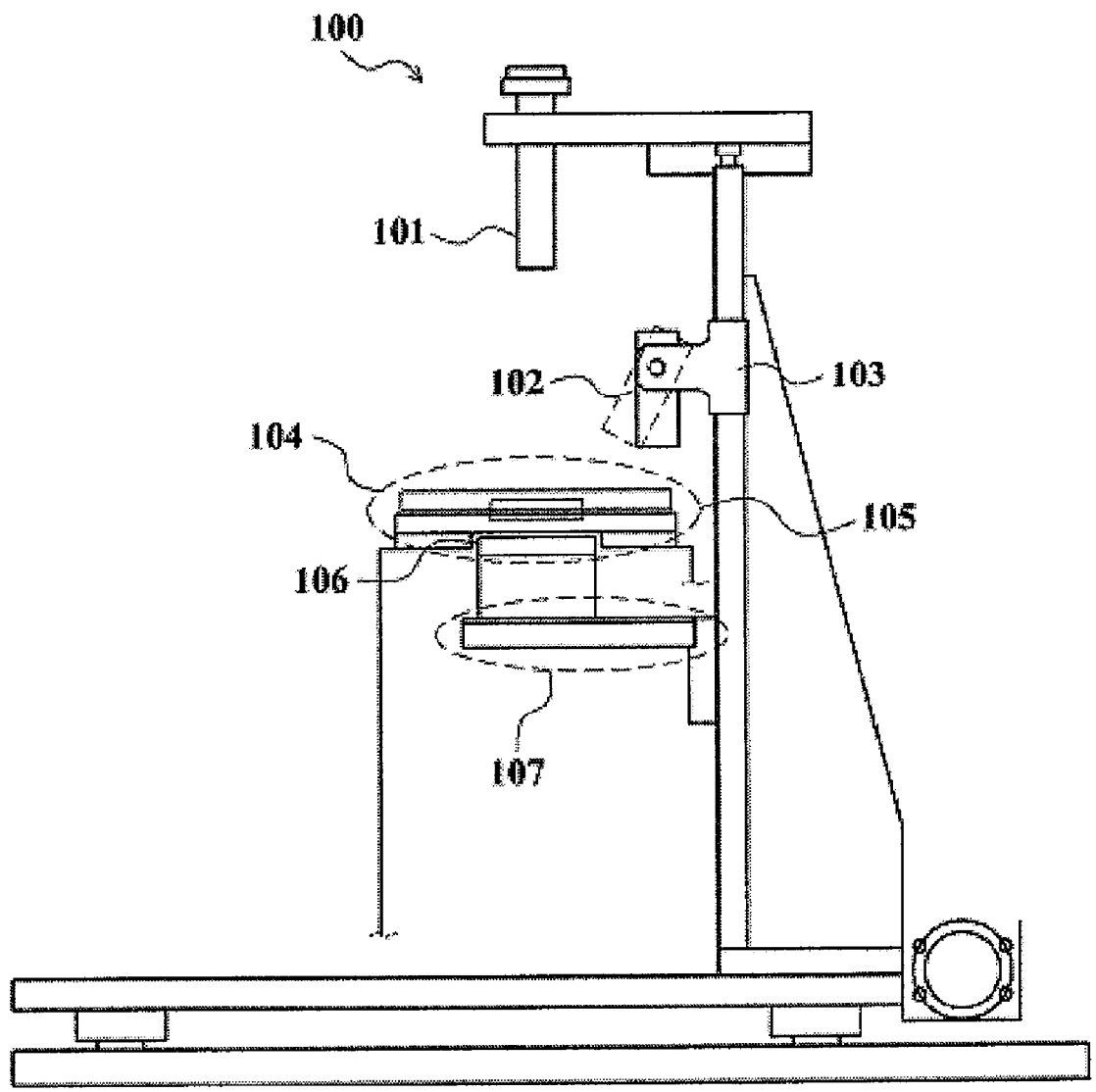
FIG. 1 is a side view of the apparatus for analyzing cells in real-time in accordance with an embodiment of the present invention.

FIG. 1 is a side view of the apparatus for analyzing cells in real-time in accordance with an embodiment of the present invention. In accordance with the present invention, the apparatus for analyzing cells in real-time comprises a platform 105 for a microplate 104 containing a sample to be placed on; an infrared ray (IR) observation unit 100; and a signal processing unit (not shown) for processing an IR signal received from the IR observation unit 100.

The microplate 104 containing a sample is mounted on the platform 105, and the platform 105 is configured to change position of the microplate 104 horizontally in the X-Y direction.

The IR observation unit 100 comprises a wavelength-tunable light source unit 102 which is installed over the sample on the platform 105; an IR sensing unit 106 for receiving IR light which has been irradiated from the wavelength-tunable light source unit and passed through the sample, the IR sensing unit being located under the platform; and an image sensing unit for alignment 101 for checking the area of the sample which is being irradiated by the light from the wavelength-tunable light source unit.

It is preferable that a wavelength-tunable light source of the wavelength-tunable light source unit 102 emits light condensed enough to irradiate only a specific cell. The wavelength-tunable light source of the wavelength-tunable light source unit 102 comprises a pumping light source and a non-linear wavelength-tunable means. At this time, the non-linear wavelength-tunable means comprises a ferroelectric substrate with a periodic polarization inversion; an optical waveguide of the ferroelectric substrate; and an electrode on the ferroelectric substrate. In this configuration, it is preferable that the wavelength of the light proceeding along the optical waveguide is changed by the electric field applied through the electrode. Such wavelength-tunable light source can be used for a long time and thus it is suitable for long-time observation of cells.

The wavelength-tunable light source unit 102 can further comprise a means for adjusting beam position of the wavelength-tunable light source, according to a type or an irradiation angle of the wavelength-tunable light source, or a size of the irradiation area.

The wavelength-tunable light source unit 102 preferably comprises a wavelength-tunable light source-moving means 103 for moving the wavelength-tunable light source vertically so as to change directions of irradiation. In addition, it is preferable that the wavelength-tunable light source unit 102 further comprises an irradiation angle-adjusting means for changing angles of irradiation in the direction perpendicular to the moving direction of the irradiation angle-adjusting means (refer to FIGS. 1 and 2). The wavelength-tunable light source unit 102 comprising the wavelength-tunable light source-moving means 103 and the irradiation angle-adjusting means can be used to irradiate any part of the whole irradiation area.

It is preferable that the wavelength-tunable light source unit 102 emits near IR light, especially having a wavelength of 700 to 1,000 nm.

The IR sensing unit needs to be configured to exactly receive the light which has been irradiated by the wavelength-tunable light source unit 102 and then passed through the sample. Accordingly, the IR sensing unit comprises a detector 106 for detecting IR and a sensor position controlling means 107 for controlling light-receiving positions of the detector 106 by moving the detector in the XYZ directions. At this time, it is preferable that the detector 106 can detect IR light with a wavelength of 550 to 1,000 nm.

It is preferable that the IR sensing unit further comprises a filter which filters the light which has passed through a sample to transmit the light with a predetermined range of wavelength to the detector 106. If light emitted from the wavelength-tunable light source unit 102 directly enters the detector 106, it is impossible to tell if a resulting signal is made by the light emitted from the wavelength-tunable light source unit 102 directly to the detector or by the light which has passed through the sample. Related to this, the filter prevents the light from the wavelength-tunable light source unit 102 from directly entering the detector and only the light which has passed through the sample is allowed to pass through the filter. The wavelength range of the light allowed to pass through the filter can be properly selected according to the wavelength of the wavelength-tunable light source unit 102 or the wavelength range of the light which has passed through the sample.

In addition, the IR sensing unit can further comprise a light condensing means for condensing the light which has passed through the filter or the sample to the IR detector.

The image sensing unit for alignment 101 is installed over the sample and comprises an imaging means and a displaying means. And the imaging means can be a charge-coupled device (CCD) camera, etc. The imaging sensing unit for alignment uses the imaging means to photograph a specific area, magnifies a photographed image, and then outputs the magnified image to the displaying means. Using the magnified image of a specific area of the sample, an operator can finely adjust the area of the sample which is being irradiated by the light emitted from the wavelength-tunable light source unit 102. For such fine adjustment, the wavelength-tunable light source moving means and the irradiation angle-adjusting means are used. As position of the wavelength-tunable light source unit 102 is changed, light-receiving position of the IR sensing unit 106 and 107 needs to be changed accordingly.

The signal processing unit processes an IR signal generated by the light which has passed though a specific cell and received by the IR sensing unit, and analyzes the IR characteristics of the cell. In this way, the apparatus for analyzing cells in real-time in accordance with the present invention enables an operator to observe IR characteristics of a specific cell according to changes in external environments, in real-time. At this time, the IR signal is preferably a digital signal.

Figure 2:
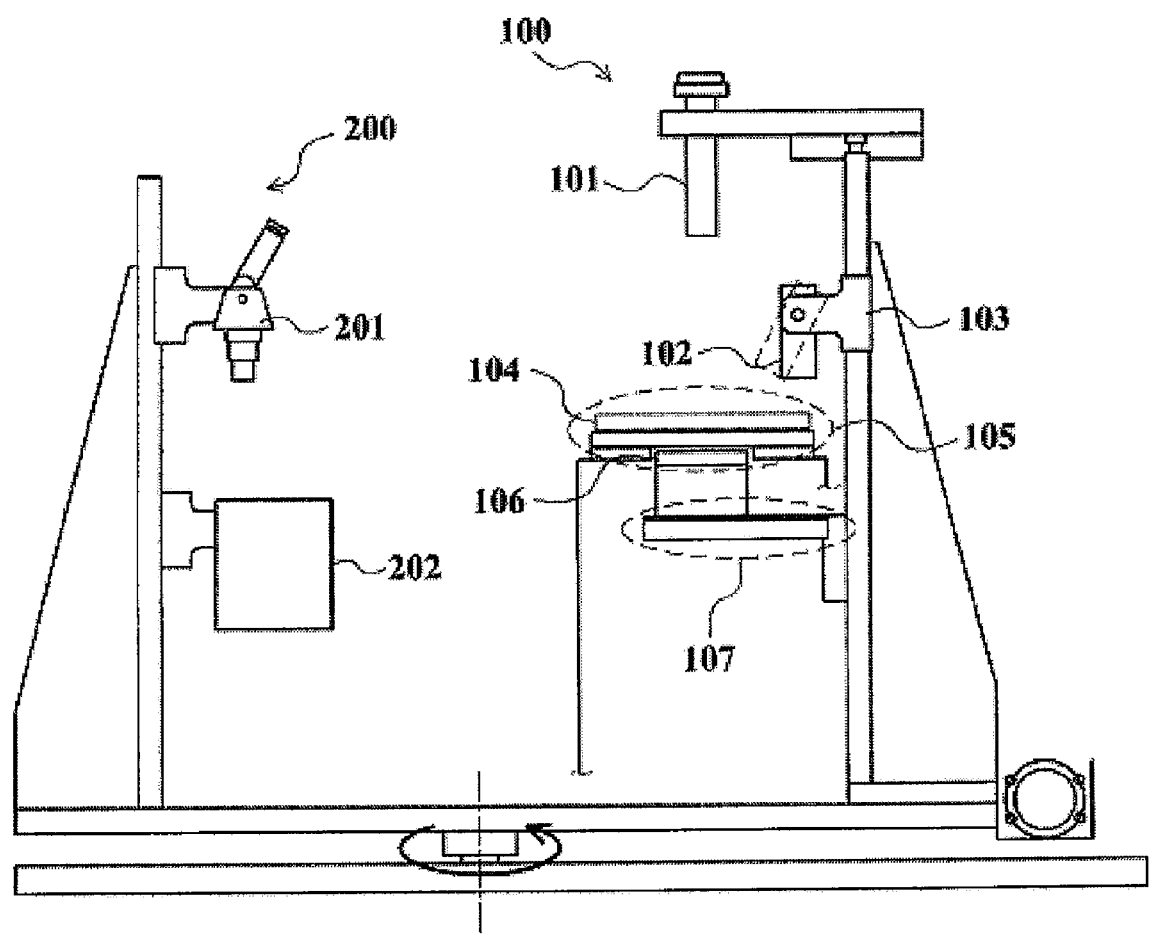
FIG. 2 is a view of the apparatus for analyzing cells in real-time, of which the units can move rotatably, in accordance with another embodiment of the present invention.

FIG. 2 is a view of the apparatus for analyzing cells in real-time, in accordance with another embodiment of the present invention. The apparatus for analyzing cells in real-time in accordance with this embodiment of the present invention has a microscope unit 200 coupled to the apparatus for analyzing cells in real-time which is described above. In this configuration, the area which is photographed by the image sensing unit for alignment 101 can be conveniently controlled. And magnifying power of the microscope unit 200 can be controlled manually or automatically.

In accordance with this embodiment of the present invention, the microscope unit 200 comprises a microscope 201 and a light source 202 for irradiating area to be observed by the microscope.

Figure 3:
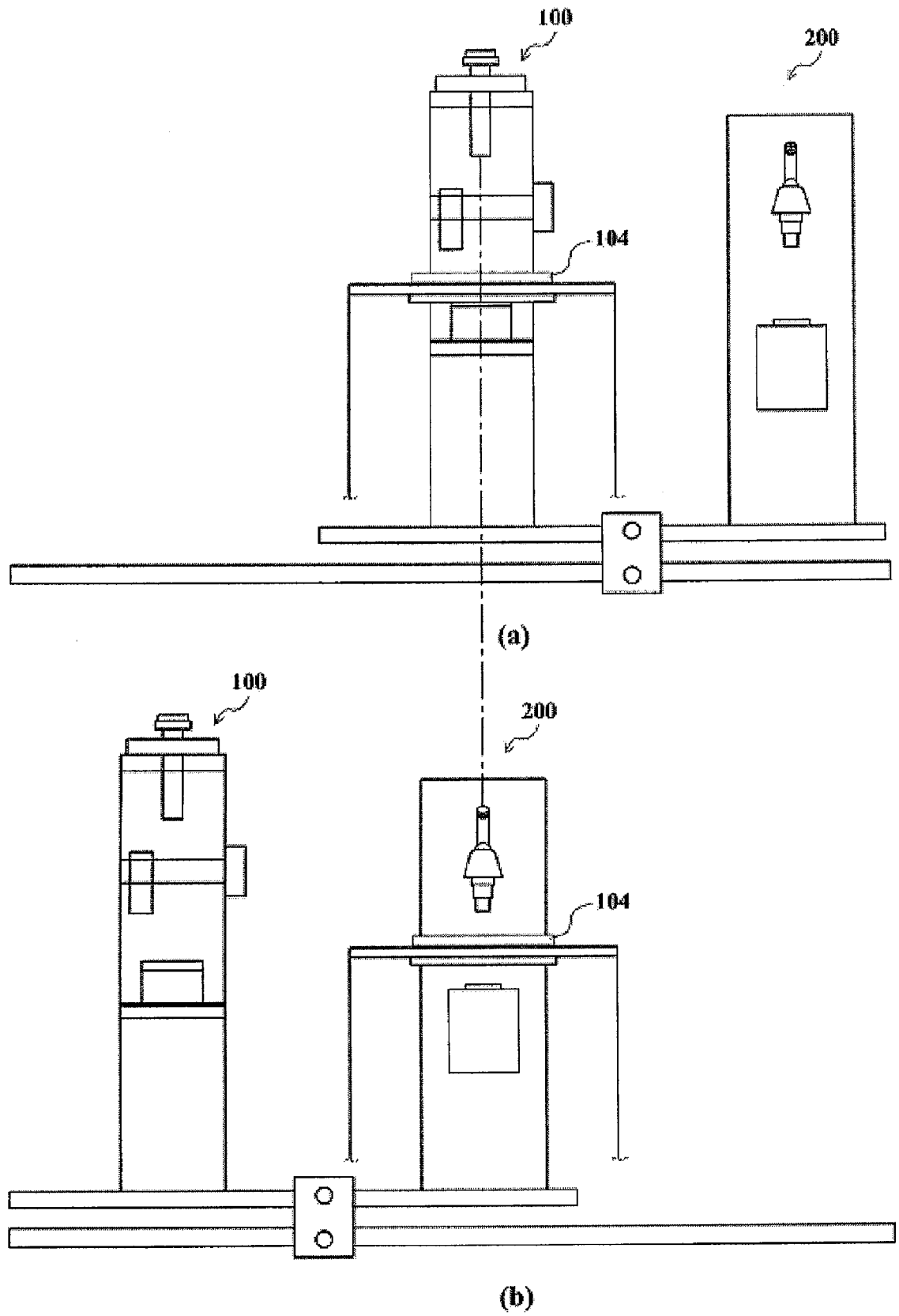
FIGS. 3a and 3b collectively show a front view of the apparatus for analyzing cells in real-time, of which the units can move horizontally, in accordance with another embodiment of the present invention.

The microscope unit 200 is coupled to the IR observation unit 100 in such a way that they can move together with a predetermined distance between them. Referring to FIGS. 2 and 3, the IR observation unit 100 and the microscope unit 200 can move simultaneously, rotatably (FIG. 2) or horizontally (FIG. 3). With such configuration, the apparatus for analyzing cells in real-time can shift from a location for microscope observation (FIG. 3(b)) to a location for IR measurement (FIG. 3(a)), and vice versa. It is preferable that the apparatus for analyzing cells in real-time in accordance with this embodiment of the present invention comprises a means for rotatable or horizontal movement of the IR observation unit 100 and the microscope unit 200.

In the location for microscope observation (FIG. 3(b)), for example, an operator can use the microscope unit 200 in the following way: an operator observes a sample under low magnifying power, and then under high magnifying power while changing positions of the platform 105 so that the part of the sample he or she is interested in can be located within the area which is being observed by the microscope unit 200. When a proper position of the platform 105 is decided, the IR observation unit 100 and the microscope unit 200 coupled to each other are shifted to the location for IR measurement (FIG. 3(a)). In the location for IR measurement, the image sensing unit for alignment 101 outputs an image of the area which was observed by the microscope unit 200. In this way, an operator can adjust irradiation area (target cell) by means of the image sensing unit for alignment 101.

The area of a sample to be observed is decided in the location for microscope observation (FIG. 3(b)), and a target, for example, a cell in the area of the sample for which a measurement will be made is decided. After that, IR measurement of the target is made. For such measurement, the apparatus for analyzing cells in real-time has been configured for the center of the sample area observed by the microscope unit 200 in the location for microscope observation (FIG. 3(b)) to be equal to the center of the area photographed by the image sensing unit for alignment 101 in the location for IR measurement.

The microscope unit can comprise an image sensor (not shown) which is located near an ocular lens; and an image processing unit (not shown) for obtaining and processing an image of a target cell through a signal received from the image sensor.

The image processing unit can comprise an image processing means. Or the image processing unit can comprise an image processing means and a subject outputting means. Here, the image processing means obtains an image through the signal received from the image sensor, and enlarges, reduces, shifts, rotates or illuminates the image or changes set-up of its backgrounds so that an operator can observe the image conveniently.

In case that the image processing unit further comprises the subject outputting means, the image obtained by the image processing means is transferred to the subject outputting means. At this time, the subject outputting means comprises a black/white conversion means for processing for the cell image to change it into a black/white image for binary processing; an individual recognizing means for recognizing individual cells by a lightness difference which occurs in the boundaries of the cell and backgrounds (cell culture solution) on the black/white image obtained by the black/white conversion means. Moreover, the subject outputting means can further comprise a recognition factor providing means. In case of plural cells being recognized, the recognition factor providing means provides each of the individual cells with a recognition factor, for example, a number or a name. In this way, the respective records of plural cells can be simultaneously observed.

In addition, the subject outputting means can further comprise a position change measuring means, which measures a center of gravity of a cell and get a migration distance of the cell from a variation of the measured center of gravity for a predetermined time. At this time, the measured center of gravity of a cell is outputted as coordinate values. Accordingly, the migration distance of a cell can be easily measured through a change in the coordinate values. Additionally, velocity or accelerated velocity of a cell can be obtained using resulting values measured through the subject outputting means.

The apparatus for analyzing cells in real-time in accordance with the present invention can further comprise a controlling unit, which controls the apparatus to track a specific cell automatically and output IR characteristics of the cell at predetermined time intervals. For example, in the location for microscope observation, the controlling unit receives information on a recognition factor which the recognition factor providing means provides for a specific individual cell; receives information on a change in the cell's positions from the position change measuring means; changes positions of the platform or the microscope unit at set time intervals or in case that the cell moves beyond a set range so that the individual cell can be located within the area observed through the microscope; and controls the apparatus to shift to the location for IR measurement at set time intervals, and then controls the wavelength-tunable light source unit to irradiate light to the individual cell and controls the signal processing unit to process an IR signal generated by the irradiation of light. In such a way, the controlling unit enables automatic observation of a cell.

In accordance with another embodiment of the present invention, in addition to the platform, the IR observation unit and the signal processing unit described above, the apparatus for analyzing cells in real-time can further comprise a controlling unit for controlling the image processing unit or the IR observation unit, wherein the image processing unit processes an image signal received from the imaging sensing unit for alignment. And a subject outputting means in accordance with this embodiment of the present invention functions in the same way as the subject outputting means according to the embodiment described above.

The apparatus for analyzing cells in real-time in accordance with this embodiment of the present invention can further comprise a controlling unit which controls the IR observation unit to track a specific cell automatically and output IR characteristics of the cell at predetermined time intervals. For example, the controlling unit receives information on a recognition factor which the recognition factor providing means provides for a specific individual cell; receives information on a change in the cell's positions from the position change measuring means; changes positions of the platform at set time intervals or in case that the cell moves beyond a set range so that the individual cell can be located within the area observed through the image sensor for alignment; and controls the wavelength-tunable light source unit to irradiate light to the cell at set time intervals and controls the signal processing unit to process an IR signal received by the IR sensing unit.

In accordance with this embodiment of the present invention, it is preferable that the apparatus for analyzing cells in real-time further comprises a microscope unit for finely adjust observation area before automatic observation, which is controlled by the controlling unit.

The apparatus for analyzing cells in real-time in accordance with the present invention has an advantage in that it can analyze signals received from the IR sensor in case of dyeing specific material of a cell with an IR reagent, and thus quantify the material. And it can be used to analyze characteristics of a cell's movement in response to a cancer cell attractant. Moreover, it can be used to analyze characteristics of a cell's movement in response to its external environments, for example, temperature, humidity, concentration of $CO_2$ or dissolved oxygen (DO), or amount of an attractant.

The apparatus for analyzing cells in real-time in accordance with the present invention has another advantage in that it can be used to observe in detail how a microorganism reacts to an antibiotic. And it can be used to observe and store images of microorganisms and their external environments in real-time during their culture, for a long time. In addition, it can be used to analyze quantitatively a real number of microorganisms in a sample by observing their migration distances. At this time, Analyses of the effects to IR can be made simultaneously.

What is claimed is:

1. An apparatus for analyzing cells in real-time comprising:
a platform for a sample to be placed on;
an infrared ray (IR) observation unit; and
a signal processing unit for processing an IR signal received from the IR observation unit,
wherein the IR observation unit comprises:
a wavelength-tunable light source unit for irradiating light to a specific area of the sample, wherein the wavelength-tunable light source unit comprises a pumping light source and a non-linear wavelength-tunable means, and the non-linear wavelength-tunable means, and the non-linear wavelength-tunable means comprise a ferroelectric substrate, an optical waveguide of the ferroelectric substrate, so that the wavelength-tunable light source unit changes the wavelength of the light by the electric field applied through the electrode;
an IR sensing unit for receiving the light which has been irradiated by the wavelength-tunable light source unit and passed through the sample, wherein the IR sensing unit comprises a filter for filtering the light which has passed through the sample to get the light within a predetermined wavelength range to pass through, a detector for receiving the light which has passed though the filter and generating the IR signal, a light condensing means for condensing the light which has passed through the filter to the detector; and
a sensor position controlling means for controlling positions of the filter, the light condensing means and the detector; and
an image sensing unit for alignment for checking the area of the sample which is being irradiated by the light from the wavelength-tunable light source unit.

2. The apparatus for analyzing cells in real-time as recited in claim 1, further comprising a microscope unit for observing the sample with,
wherein the microscope unit and the IR observation unit are coupled to each other in such a way that they can move together, separated in a predetermined distance from each other, between a location for microscope observation and a location for IR measurement, the location for microscope observation being for the microscope to observe the sample and the location for TR measurement being for the IR observation unit to measure the sample.

3. The apparatus for analyzing cells in real-time as recited in claim 2, wherein the area of the sample which is observed by the microscope unit in the location for microscope observation has the same center as that of the area which is photographed by the image sensing unit for alignment in the location for IR measurement.

4. The apparatus for analyzing cells in real-time as recited in claim 2, further comprising:
an image sensor which coupled to an ocular lens of the microscope unit; and
an image processing unit for processing an image signal received from the image sensor.

5. The apparatus for analyzing cells in real-time as recited in claim 4, wherein the image processing unit comprises:
a black/white conversion means for binary processing of an image of cells in the sample obtained from the image signal;
an individual recognizing means for recognizing the individual cells by a lightness difference in the boundaries of the image which has been black/white conversed by the black/white conversion means; and a recognition factor providing means for providing a recognition factor to each of the individual cells which have been recognized by the individual recognizing means.

6. The apparatus for analyzing cells in real-time as recited in claim 5, further comprising a position change measuring unit for measuring a change in the cell's position using a variation in values of its center of gravity, from the image processed in the image processing unit.

7. The apparatus for analyzing cells in real-time as recited in claim 6, further comprising a controlling unit, wherein the controlling unit receives information on a recognition factor which the recognition factor providing means provides for a specific individual cell and receives information on a change in the cell's position from the position change measuring means;

changes positions of the platform or the microscope unit at set time intervals or in case that the cell moves beyond a set range so that the individual cell can be located within the area observed using the microscope unit; and controls the wavelength-tunable light source unit to irradiate light to the individual cell in the location for IR measurement at set time intervals and controls the signal processing unit to process an IR signal.

\* \* \* \* \*